(12) United States Patent
Feng et al.

(10) Patent No.: US 12,420,055 B1
(45) Date of Patent: Sep. 23, 2025

(54) METHOD OF PREPARING URINARY CATHETER HAVING BALLOON OF THREE CAVITIES AT TOP END OF URINARY CATHETER

(71) Applicant: WUXI SECOND PEOPLE'S HOSPITAL, Jiangsu (CN)

(72) Inventors: Ninghan Feng, Jiangsu (CN); Yuwei Zhang, Jiangsu (CN); Yangkun Feng, Jiangsu (CN); Ye Hua, Jiangsu (CN); Yang Wang, Jiangsu (CN); Menglu Li, Jiangsu (CN); Peng Jiang, Jiangsu (CN); Yang Shen, Jiangsu (CN); Bo Liu, Jiangsu (CN)

(73) Assignee: WUXI SECOND PEOPLE'S HOSPITAL, Wuxi (CN)

( * ) Notice: Subject to any disclaimer, the term of this patent is extended or adjusted under 35 U.S.C. 154(b) by 0 days.

(21) Appl. No.: 19/003,698

(22) Filed: Dec. 27, 2024

(30) Foreign Application Priority Data

May 1, 2024 (CN) .......................... 202410546002.4

(51) Int. Cl.
*A61M 25/00* (2006.01)
*A61M 25/10* (2013.01)

(52) U.S. Cl.
CPC ...... *A61M 25/001* (2013.01); *A61M 25/0017* (2013.01); *A61M 25/10* (2013.01)

(58) Field of Classification Search
None
See application file for complete search history.

(56) References Cited

U.S. PATENT DOCUMENTS

| 4,958,634 A | 9/1990 | Jang |
| 5,569,184 A | 10/1996 | Crocker et al. |

OTHER PUBLICATIONS

Notification to Grant Patent Right for Invention, Chinese Application No. 202410546002.4, mailed Nov. 14, 2024 (3 pages).
CNIPA, Office Action issued for Chinese Application No. 202410546002.4, mailed Sep. 7, 2024 (7 pages).

*Primary Examiner* — Christopher T Schatz
(74) *Attorney, Agent, or Firm* — HOWARD M COHN and Associates, LLC

(57) ABSTRACT

A method of preparing a urinary catheter having a balloon of three cavities at a top end thereof includes: step 1, preparing a catheter having one urinary guiding cavity and three water injection cavities, cutting two ends of the catheter to be flat; step 2, cutting from a top end of the catheter having the four cavities from the catheter longitudinally to form three separated catheters, each having one second cavity, closing a top end of each of the three catheters; step 3, hot-pressing the three catheters by placing the three catheters in a steel plate for 40° C. to 60° C. and 5 min to 15 min at 5 kg to 7.5 kg, trimming the outer wall of the catheters; step 4, connecting top ends of the catheters to each other, taking a guide thread to pass through the urinary guiding cavity to be connected to the top ends of the catheters.

4 Claims, 8 Drawing Sheets

METHOD OF PREPARING URINARY CATHETER HAVING BALLOON OF THREE CAVITIES AT TOP END OF URINARY CATHETER

TECHNICAL FIELD

Embodiments of the present disclosure relate to a technical field of urinary catheters, and particularly, to a gun container having a method of preparing a urinary catheter having a balloon of three cavities at a top end of the urinary catheter.

BACKGROUND

A Chinese patent (application No. 202410335744.2) provides a catheter device arranged with a ballon at a top end of a catheter, and the balloon has three cavities. Compared to the related art, a technical solution in the above Chinese patent has a variety of clinically beneficial technical effects. However, in a technical field of preparing catheters, no balloon is arranged at the top end of the catheter. In the related art, only one balloon is arranged on a side wall of the catheter, and the one balloon is glued to the side wall. A preparing process of the catheter is complicated. Therefore, a method of glueing the balloon on the side wall of the catheter is unsuitable for preparing the catheter device, which is provided in the Chinese patent application No.: 202410335744.2 and has the balloon of three cavities at the top end of the catheter.

Therefore, a process of quickly arranging the balloon having three cavities to the top end of the catheter needs to be provided.

SUMMARY

The present disclosure provides a method of preparing a urinary catheter having a balloon of three cavities at a top end of the urinary catheter.

The Chinese patent application No.: 202410335744.2 provides a urinary catheter device including following components.

A tube body defines a urinary guiding cavity and a plurality of balloon injection cavities inside the tube body.

At least three columnar balloons are arranged. When the at least three columnar balloons are emptied, each of the at least three columnar balloons is irregularly elongated. When the at least three columnar balloons are bulging, each of the at least three columnar balloons is elliptical. The at least three columnar balloons are connected to each other at one end of each of the at least three columnar balloons. The other end of each of the at least three columnar balloons has an injection opening. The injection opening of each of the at least three columnar balloons is communicated to one respective balloon injection cavity of the plurality of balloon injection cavities.

An outer shell is arranged. An end of the outer shell is a guide portion, and the other end of the outer shell is connected to a top end of the tube body. The outer shell wraps around an outer side of each of the at least three columnar balloons. The outer shell defines an opening. The at least three columnar balloons, when being bulging, are capable of bursting the outer shell.

A guide thread is arranged. An end of the guide thread is connected to a top end of each of the at least three columnar balloons. The guide thread passes through at least a portion of the urinary guiding cavity, and the other end of the guide thread extends to an outer side of the tube body.

Embodiments of the present disclosure provide a method of preparing a urinary catheter to quickly prepare a large number of urinary catheters, where each of the urinary catheters is arranged with a balloon having three cavities at a top end thereof.

Step 1, a conventional catheter having four cavities is firstly prepared (a diameter of the tube body, a length of the tube body, and a material of the tube body are all available in the related art). A first cavity of the four cavities is located at a circular center of the tube body and has a diameter of 2 mm. The first cavity serves as the urinary guiding cavity. The other three cavities of the four cavities are surrounding the first cavity. The other three cavities serve as three second cavities and serve as three water injection cavities. Each of the three second cavities has a diameter of 0.5 mm. A circular center of each of the three second cavities is located at a center of a circular radius of a cross section of the catheter having the four cavities. A connection line connecting circular centers of the three second cavities forms an equilateral triangle. A center/pendant center of the equilateral triangle is a circular center of the first cavity. The step 1 is usually achieved by performing a mold extrusion method (available in the related art), which is the fastest and simplest method. Of course, other methods are available. For example, the Chinese patent application No. CN202011379002.8 provides a process of molding a double-cavity catheter and a double-cavity catheter. For the process of molding the double-cavity catheter, a sleeve tube is provided, and heating and melting are performed to obtain a one-piece silicone catheter having a plurality of cavities. Two ends of the catheter having the four cavities are trimmed to be flat.

Step 2, 2 cm from a top end of the catheter having the four cavities is separated from the catheter longitudinally (along a length direction of the catheter), three catheters separated from each other are obtained, and each of the three catheters has a single cavity. A top end of each of the three catheters, each having the single cavity, is closed. The top end of each of the three catheters refers to an end point away from an un-trimmed end of the catheter having the four cavities.

Step 3, each of the three catheters, each having the single cavity, is hot-pressed to be flat. In detail, each of the three catheters, each having the single cavity, is placed into a steel plate, where a front and a rear of the steel plate can supply a pressure and heat. A temperature of hot-pressing is 40° C. to 60° C., and a duration of hot-pressing is 5 minutes to 15 minutes. A pressure value applied to each of the three catheters, each having the single cavity, is 5 kg to 7.5 kg. In this way, each of the three catheters, each having the single cavity, is pressed to be flat. A redundant portion of an outer wall of each of the three catheters is trimmed to enable each of the three catheters to have a wall thickness of 0.5 mm. Apparently, in this case, a top portion of each of the three separated catheters, each having the single cavity, becomes longer; an inner hollow portion of each of the three separated catheters becomes wider; and an edge of the outer wall of each of the three separated catheters becomes wider. In this case, a hollow portion of the top portion of each of the three separated catheters, each having the single cavity, becomes longer and wider to form a shape of a balloon. At this moment, an internal configuration of each of the three catheters, each having the single cavity, is similar to an elongated balloon. Therefore, each of the three catheters, each having the single cavity, can be recorded/referred to as the balloon accordingly. After hot-pressing, the redundant portion of the outer wall of each of the three catheters, each having the single cavity, is trimmed, and the outer wall of each of the three catheters is thinner, but the outer wall is not damaged. On the one hand, a volume of the balloon is reduced, and therefore, the balloon can be fit into an outer shell easily. On the other hand, the balloon may be expanded easily when being filled with water. After the outer wall is thinned, rigidity of the outer wall is reduced, a stress is relieved, the outer wall can be deformed more easily when being filled with water. When each of the three catheters is hot-pressed to be flat, it is convenient for a human operator or a machine to trim the outer wall to be as thin as 0.5 mm. Each of the three catheters, each having the single cavity, has an original cylindrical configuration. On the one hand, a cylindrical outer wall may not be manually trimmed to be thin easily. On the other hand, it is difficult to manually trim the outer wall to have the thickness of 0.5 mm, the outer wall may be damaged easily. In the following, a mold is used to trim the outer wall, and in this way, the outer wall is not trimmed manually, and configuration of the outer wall may not be damaged easily.

Step 4, top ends (the closed top ends) of the three catheters, each having the single cavity, are connected to each other by glue or by hot-melting. A guide thread (usually a metal thread) is taken to pass through the urinary guiding cavity. The guide thread enters the urinary guiding cavity from a tail end of the urinary guiding cavity and extends out of the urinary guiding cavity from a top portion (referring to an end near the balloon) of the urinary guiding cavity. The guide thread is connected to the top portion of each of the three catheters, each having the single cavity.

Step 5, a water-soluble polymer is used to be pressed to form a shape of the outer shell in a corresponding mold. A tail end of the outer shell is coated with polymer glue, and the balloon is collected inside the outer shell. The tail end of the outer shell is glued to a top portion of the catheter having the four cavities. In order to enable the glue to be applied smoothly, top portion of the catheter having the four cavities may be arranged to have a slope in advance.

Further, it is obviously seen that, the three catheters, each having the single cavity and having the outer wall, in the step 2 are manually separated; and the outer wall of each of the three catheters, each having the single cavity, is trimmed to be thinned manually. The step 2 and the step 3 are performed manually. On the one hand, manual operation is slow. On the other hand, the manual operation has poor precision. During trimming, the outer wall of each of the three catheters, each having the single cavity, may be broken, and therefore, a mold preparing process needs to be provided.

In order to trim to obtain each of the three catheters/balloons, each having the single cavity, using a mold in the step 2 and the step 3, following molds are firstly configured.

A separation mold is configured. The separation mold includes a separation mold body. The separation mold body is a disk that move forwardly and backwardly. The separation mold body includes three separating tubes (for trimming to obtain the three catheters/balloons, each having the single cavity). Each of the three separating tubes is a hollow tubular cutter that is arranged vertically on an upper surface of the disk of the mold body. A circular center of the hollow tubular cutter corresponds to the circular center of a respective one of the three second cavities. A diameter of the hollow tubular cutter is 1 mm greater than the diameter of the respective one of the three second cavities. An opening end of each of the three separating tubes is a sharp blade, and a length of each of the three separating tubes is determined according to a length of the balloon, and in some embodiments, the length is 2 cm to 3 cm.

A hot-pressing mold is configured. The hot-pressing mold includes a hot-pressing mold body. The hot-pressing mold body is a disk that move forwardly and backwardly. A heating component is arranged inside the disk. The hot-pressing mold body includes three hot-pressing blocks configured to hot-press the three catheters, each having the single cavity. Each of the three hot-pressing blocks includes a forward hot-pressing plate and a rear hot-pressing plate, which are arranged perpendicular to an upper surface of the disk of the hot-pressing mold body. A geometric center of each set of hot-pressing plates (a center of a rectangle formed by the forward hot-pressing plate and the rear hot-pressing plate) is aligned to the circular center of a respective one of the three second cavities. The forward hot-pressing plate and the rear hot-pressing plate may be heated by the hot-pressing mold body, compressed towards each other, and adjusted. In this way, the respective one of the three catheters, each having the single cavity, disposed between the forward hot-pressing plate and the rear hot-pressing plate is applied with the pressure (available in the related art, for example, chuck fingers or hydraulic tongs of a lathe can latch a workpiece to apply adjustable pressures). A length of each of the forward hot-pressing plate and the rear hot-pressing plate is determined according to the length of the balloon, in some embodiments, the length is 2 cm to 3 cm.

Step 2, the circular center of each of the three second cavities of the catheter having the four cavities, which is obtained in the step 1, is aligned to the circular center of the respective one of the three separating tubes in the separation mold. The catheter having the four cavities is moved into the separation mold to reach 2 cm. In this case, the three separating tubes naturally separates 2 cm from the catheter having the four cavities along the length direction of the catheter to form the three catheters, each having the single cavity; and each of the three catheters, each having the single cavity, has the outer wall in the thickness of 0.5 mm.

The redundant portion of each of the three catheters, each having the single cavity, is trimmed (in this case, it is only needed to cut off the first cavity connected with the body portion of the catheter having the four cavities and cut off 2 cm of redundant silicone/rubber matrix at a root of each of the three catheters, each having the single cavity. Surrounding burrs need to be trimmed to be smooth and flat. Precision of trimming in the present step is not required. Compared to the above manual trimming, in which the outer wall of each of the three catheters, each having the single cavity, needs to be trimmed to be 0.5 mm, trimming in the present step has a greatly improved speed and precision.

Step 3, each of the three catheters, each having the single cavity, is placed between the forward hot-pressing plate and the rear hot-pressing plate. The temperature, the duration, and the pressure are adjusted as described in the above, until each of the three catheters, each having the single cavity, is hot-pressed to be flat. It can be obviously seed that, the top portion of each of the three catheters, each having the single cavity, becomes longer; the inner hollow portion of each of the three catheters becomes wider. After hot-pressing, an original configuration of each of the three catheters, each having the single cavity (has become three balloons, each having the single cavity), is damaged. The outer wall of each of the three catheters, each having the single cavity, become loose. At this moment, each of the three catheters, each having the single cavity, can be easily deformed when being injected with water.

Step 4, the rest steps are the same as the above steps.

According to the present disclosure, a manual preparation method is provided to arrange the balloon of three cavities at the top end of the conventional urinary catheter. On the basis of the manual preparation, the special molds are used for preparation. On the one hand, manual work intensity is reduced. On the other hand, in a stage of separating the three catheters, each having the single cavity, and trimming the outer wall of each of the three catheters to be thinner, the speed and the precision are greatly improved.

DETAILED DESCRIPTIONS

Figure 1:
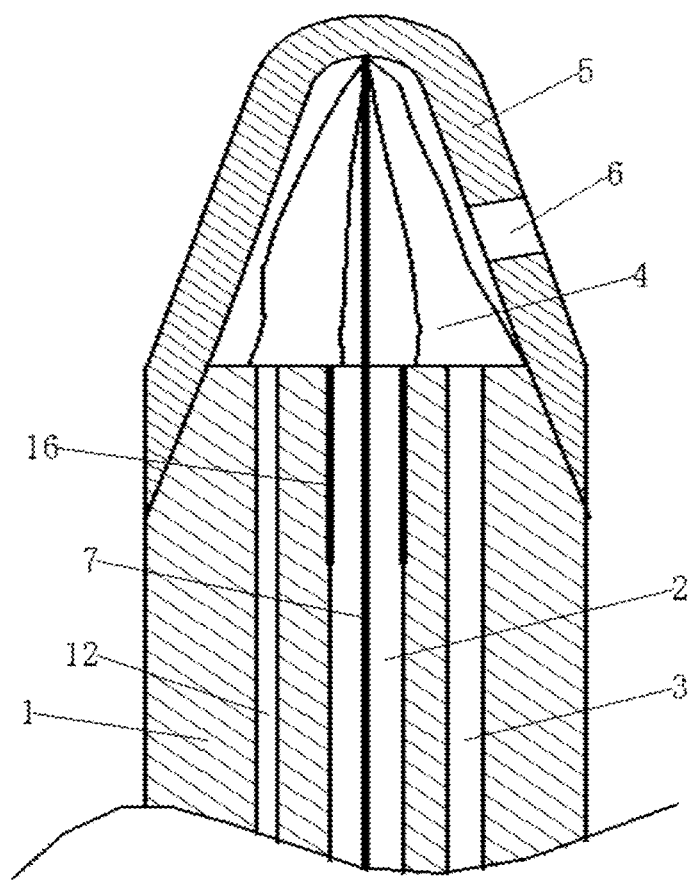
FIG. 1 is a cross-sectional view of a to-be-prepared urinary catheter having a balloon of three cavities at a top end of the urinary catheter, according to embodiments of the present disclosure.

As shown in FIG. 1, FIG. 1 shows a cross-sectional view of a to-be-prepared urinary catheter having a balloon of three cavities at a top end of the urinary catheter, according to embodiments of the present disclosure. As can be seen from FIG. 1, when a balloon 4 is directly glued to a top end of a cavity 3 (similar to a catheter 12 and a catheter 8 in FIG. 2, a diameter of a cavity 2 is larger, however, the cavity 2 is a urinary guiding cavity, and therefore, the balloon cannot be glued to a top end of the cavity 2). In addition to considering airtightness (watertightness), since an overall diameter of the catheter is relatively small (generally 3 mm to 6 mm), when a bottom of a balloon having a diameter less than 1 mm is directly glued to the top end of the cavity 3 having a diameter of less than 0.5 mm, it is difficult to align the bottom of the balloon to the top end of the cavity 3, and alignment is inefficient and is less likely to be successful. Therefore, the present disclosure provides a process of preparing the urinary catheter having the balloon of three cavities at the top end of the urinary catheter.

Embodiment 1 (Manual Trimming)

On the basis a conventional urinary catheter, the present embodiment of the present disclosure provides a method of quickly preparing a large number of urinary catheters, where each of the urinary catheters is arranged with the balloon having three cavities at the top end thereof.

Step 1, as shown in FIG. 1, a conventional catheter having four cavities is firstly prepared. A material of the catheter is silicon or rubber or any polymeric material. A diameter of each of the four cavities is referred to the above description. A first cavity of the four cavities is the urinary guiding cavity and is thicker than each of the other three cavities of the four cavities, where the other three cavities serve as three water injection cavities 12, 3, and 8. To be noted that, in the present disclosure, the first cavity, each of the three water injection cavities 12, 3, and 8, and one catheter having one single cavity refer to a same object, different terms are used based on different configurations at different preparing stages. The present step is achieved by performing an extrusion method, which is the fastest and simplest method. Two ends of the catheter 1 having the four cavities, which is obtained by performing the extrusion method, are trimmed to be flat.

Figure 2:
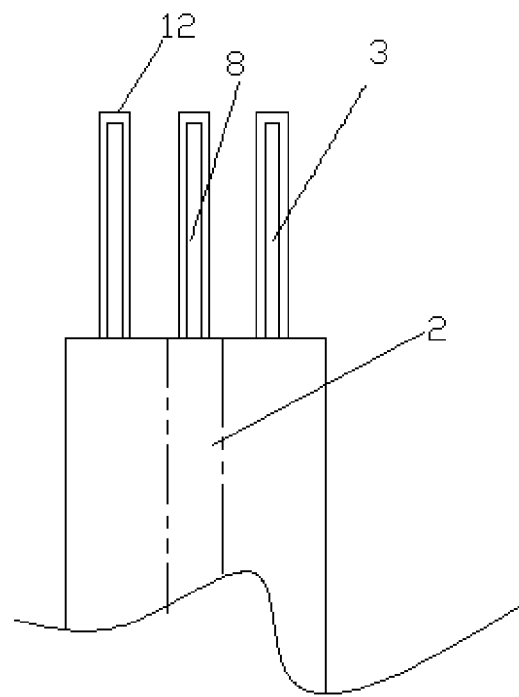
FIG. 2 is a side plane view of three water injection cavities in a conventional catheter having four cavities being cut and separated, according to embodiments of the present disclosure.
Figure 3:
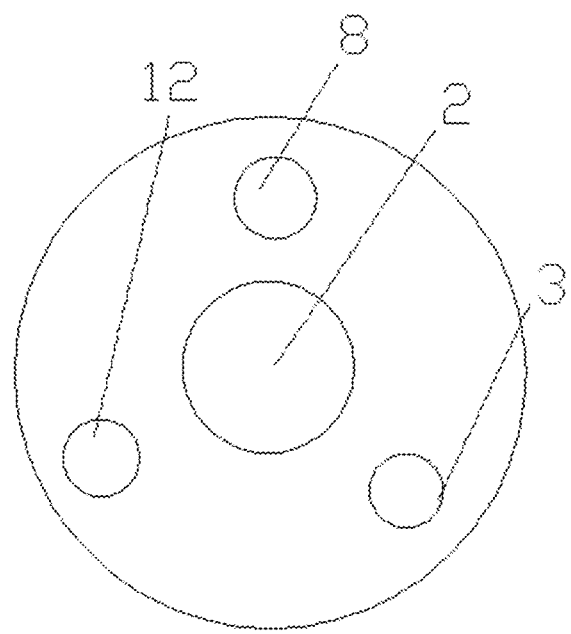
FIG. 3 is a top plane view of the three water injection cavities in the conventional catheter having the four cavities being cut and separated, according to embodiments of the present disclosure.

Step 2, as shown in FIG. 2 and FIG. 3, 2 cm from a top end of the catheter 1 is separated from the catheter 1 longitudinally (along a length direction of the catheter), where the top end refers to an end near the balloon, which will be formed in subsequent steps. The three catheters 12, 8, and 8 are referred to as three second cavities and are cut to be separated from each other, forming three catheters 12, 3, and 8, and each of the three catheters has a single cavity and a respective outer wall. A top end of each of the three catheters 12, 3, and 8, each having the single cavity, is closed. The first cavity, which is connected with a body portion of the catheter 1; and 2 cm of redundant silicone/rubber matrix at a root of each of the three catheters 12, 3, and 8, each having the single cavity, are cut off. Surrounding burrs are trimmed to be smooth and flat. A configuration as shown in FIG. 2 is obtained.

Figure 4:
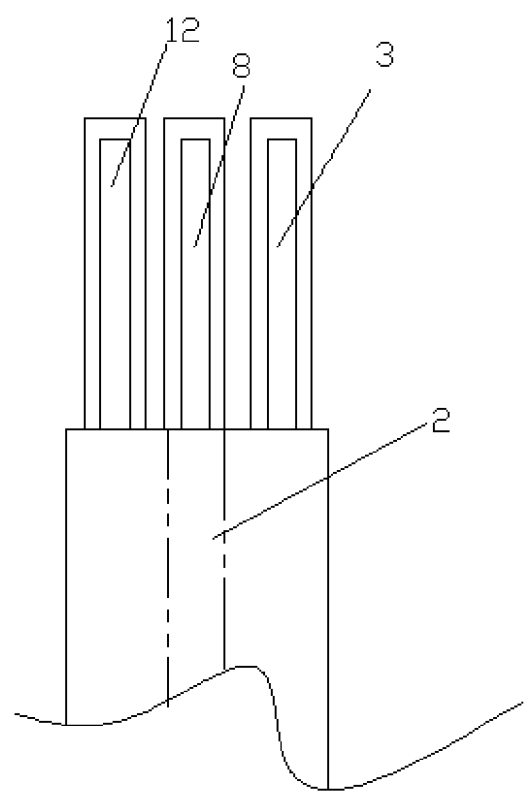
FIG. 4 is a side plane view of the three cavities being hot-pressed, according to embodiments of the present disclosure.
Figure 5:
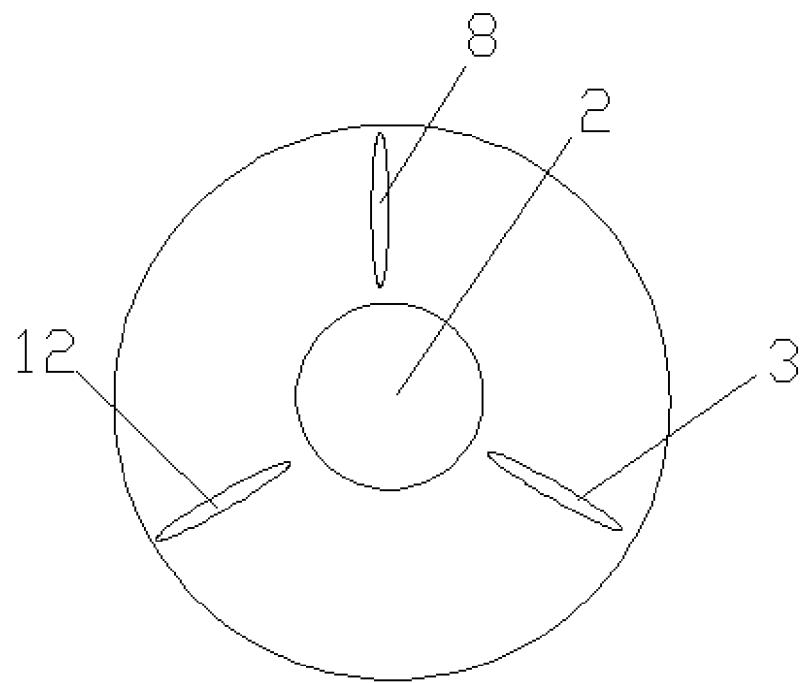
FIG. 5 is a top plane view of the three cavities being hot-pressed, according to embodiments of the present disclosure.

Step 3, as shown in FIG. 4 and FIG. 5, each of the three catheters 12, 3, and 8, each having the single cavity, is hot-pressed. A mature hot-pressing method is available in the art. When the hot-pressing is performed manually instead of using any mold, each of the three catheters 12, 3, and 8, each having the single cavity, is placed into a steel plate, where a front and a rear of the steel plate can supply a pressure and heat. A temperature of the hot-pressing is low and does not exceed 40° C. to 60° C., and a duration of the hot-pressing does not exceed 5 minutes to 15 minutes. The pressure is applied manually, each of the three catheters 12, 3, and 8, each having the single cavity, has a surface subjected to the pressure, and the surface has an area of 1 cm*0.5 cm*3.14 (radius*3.14*length). A pressure applied to the surface is 5 kg to 7.5 kg. In this way, each of the three catheters 12, 3, and 8, each having the single cavity, is pressed to be flat. Apparently, in this case, a top portion of each of the three separated catheters 12, 3, and 8, each having the single cavity, becomes longer; an inner hollow portion of each of the three separated catheters 12, 3, and 8 becomes wider; and an edge of the outer wall of each of the three separated catheters 12, 3, and 8 becomes wider. In this case, a hollow portion of each of the three separated catheters 12, 3, and 8, each having the single cavity, becomes longer and wider to form the balloon, which is labeled as the balloon 4 in FIG. 1. A redundant portion of the outer wall of each of the three catheters 12, 3, and 8 is trimmed to enable the outer wall of each of the three catheters 12, 3, and 8 to have a thickness of 0.5 mm, but the outer wall is not damaged. On the one hand, a volume of the balloon 4 is reduced, and therefore, the balloon can be fit into an outer shell 5 easily. On the other hand, the balloon may be expanded easily when being filled with water. After the outer wall is thinned, rigidity of the outer wall is reduced, and the outer wall can be deformed more easily when being filled with water. When each of the three catheters is hot-pressed to be flat, it is convenient for a human operator or a machine to trim the outer wall to be thinner. Each of the three catheters 12, 3, and 8, each having the single cavity, has an original cylindrical configuration. The cylindrical outer wall may not be manually trimmed to be thin easily.

Step 4, top ends of the three catheters 12, 3, and 8, each having the single cavity, are connected to each other by glue or by hot-melting. A guide thread 7 (usually a metal thread) is taken to pass through the urinary guiding cavity 2. The guide thread 7 enters the urinary guiding cavity 2 from a tail end (an end away from the balloon) of the urinary guiding cavity and extends out of the urinary guiding cavity from a top portion of the urinary guiding cavity. After extending out of the urinary guiding cavity 2, the guide thread 7 is connected to the top ends of the three catheters 12, 3, and 8, each having the single cavity, as shown in FIG. 1.

Figure 10:
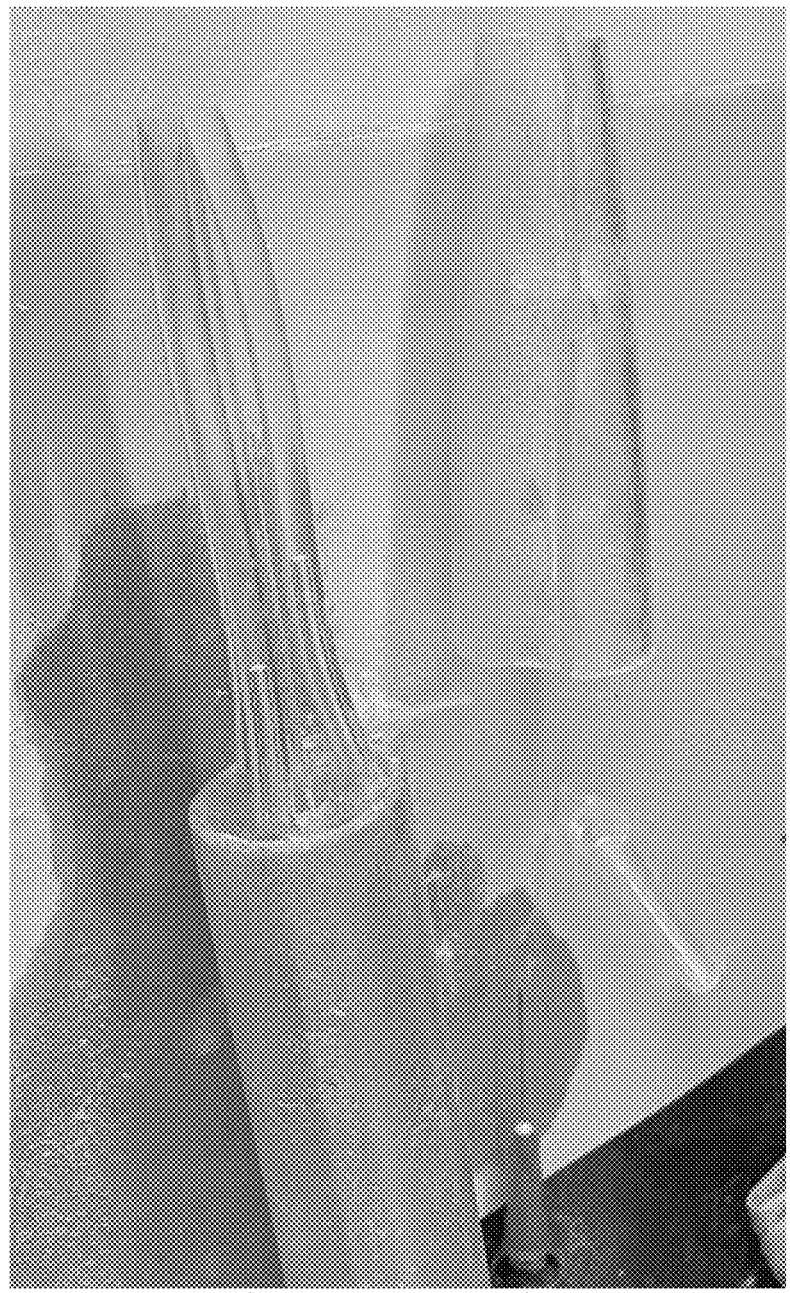
FIG. 10 is a photograph of three catheters 12, 3, and 8 and an outer shell 5, prepared based on an embodiment 1 and before being assembled to each other.
Figure 11:
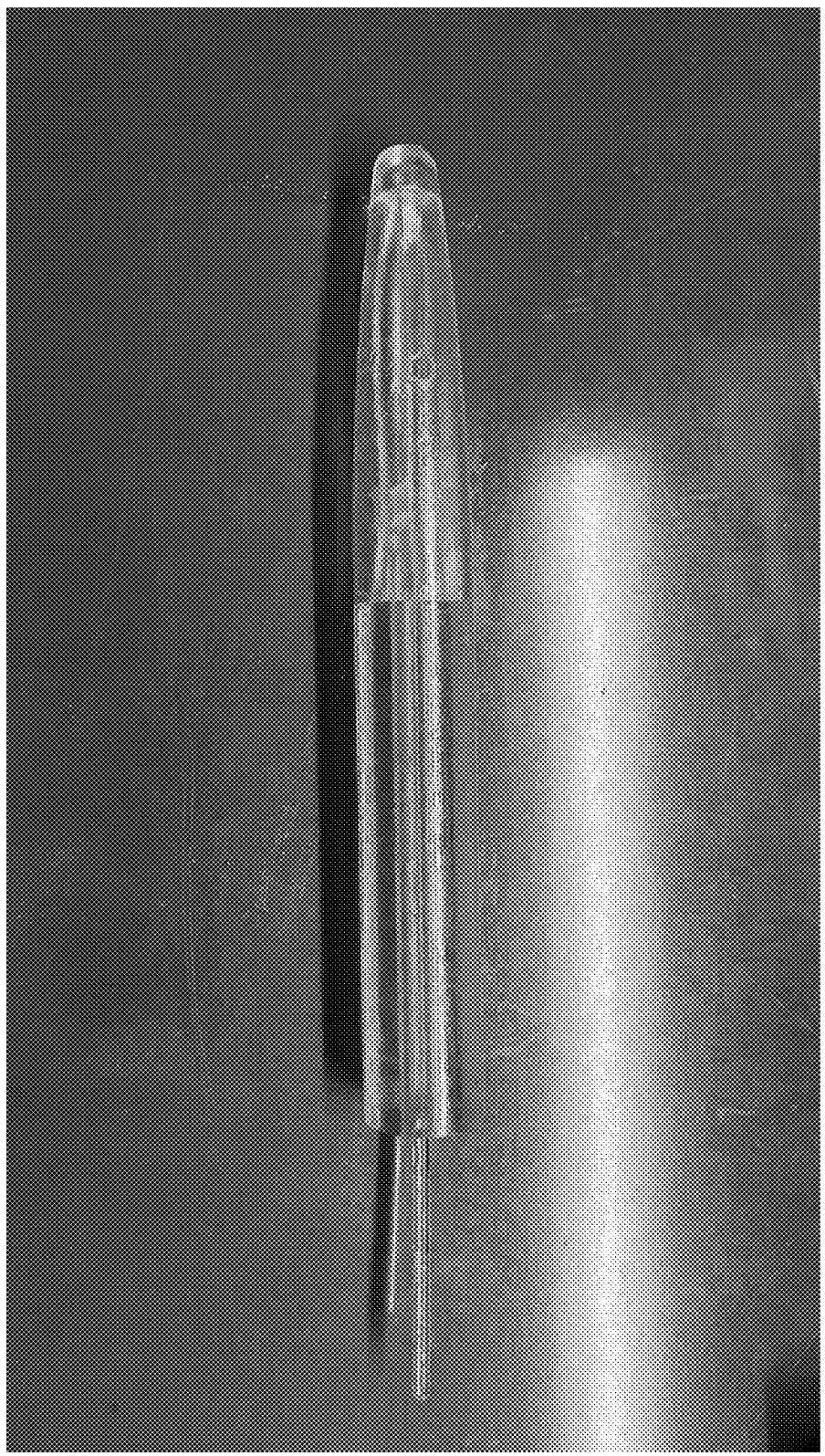
FIG. 11 is a photograph of the three catheters 12, 3, and 8 and the outer shell 5, being glued to and assembled to each other.

Step 5, as shown in FIG. 10 and FIG. 11, a water-soluble polymer (available in the art, such as degradable materials and a package made from degradable materials disclosed in the Chinese patent application No. CN201580057942.6, and multilayer water dispersible products disclosed in the U.S. patent application No. 62/926,293) is used to be pressed to form a shape of the outer shell 5, as shown in FIG. 1, in a corresponding mold. The outer shell 5 has a simple shape, and a pressing process for preparing the outer shell 5 is mature. In brief, in order to form the outer shell 5 having a missile head shape, two missile-head shaped molds are prepared. After stacking the two missile-head shaped molds, a space is defined between the two missile-head shaped molds. A shape of the space is the shape of the outer shell 5. The water-soluble polymer is injected the into the space. After dried, the water-soluble polymer is released from the mold to serve as the outer shell 5. After air-drying, the outer shell 5 can be assembled. A blow-molding process may alternatively be performed, however, precision of the blow-molding process is poorer, and mold pressing has high precision. A tail end of the outer shell 5 is coated with polymer glue, and the balloon 4 is collected inside the outer shell 5. The tail end of the outer shell 5 is glued to the top end of the catheter 1 having the four cavities. In order to enable the glue to be applied smoothly, the top end of the catheter 1 having the four cavities may be arranged to have a slope in advance.

Embodiment 2 (Trimming by Molds)

According to the Embodiment 1, it is obviously seen that, the three catheters 12, 3, and 8, each having the single cavity and having the outer wall, in the step 2 are manually separated; and the outer wall of each of the three catheters 12, 3, and 8, each having the single cavity, is trimmed to be thinned manually in the step 3. On the one hand, manual separation and trimming is slow. On the other hand, the manual separation and trimming has poor precision (it is difficult to trim the outer wall to have the thickness of 0.5 mm). During trimming, the outer wall of each of the three catheters 12, 3, and 8, each having the single cavity, may be broken, and therefore, a mold preparing process needs to be provided.

In order to trim to obtain, by using a mold, each of the three catheters 12, 3, and 8, each having the single cavity, in the step 2 and the step 3, following molds are firstly configured.

Figure 6:
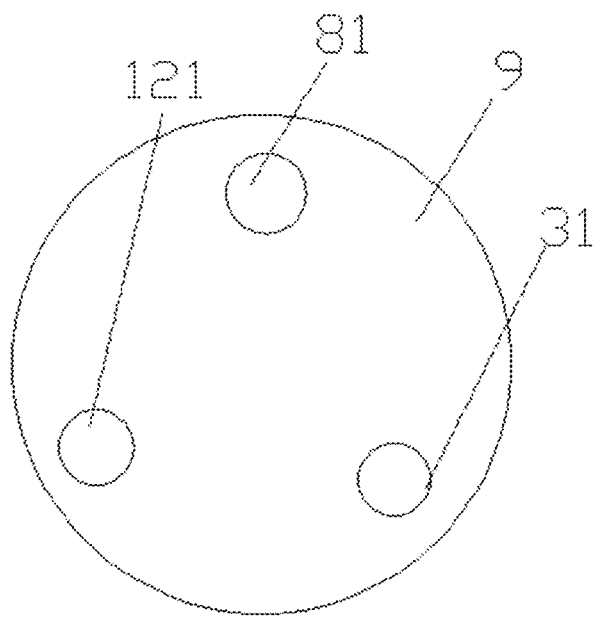
FIG. 6 is a top plane view of a separation mode for preparing three separated catheters, each having a single cavity, according to embodiments of the present disclosure.
Figure 7:
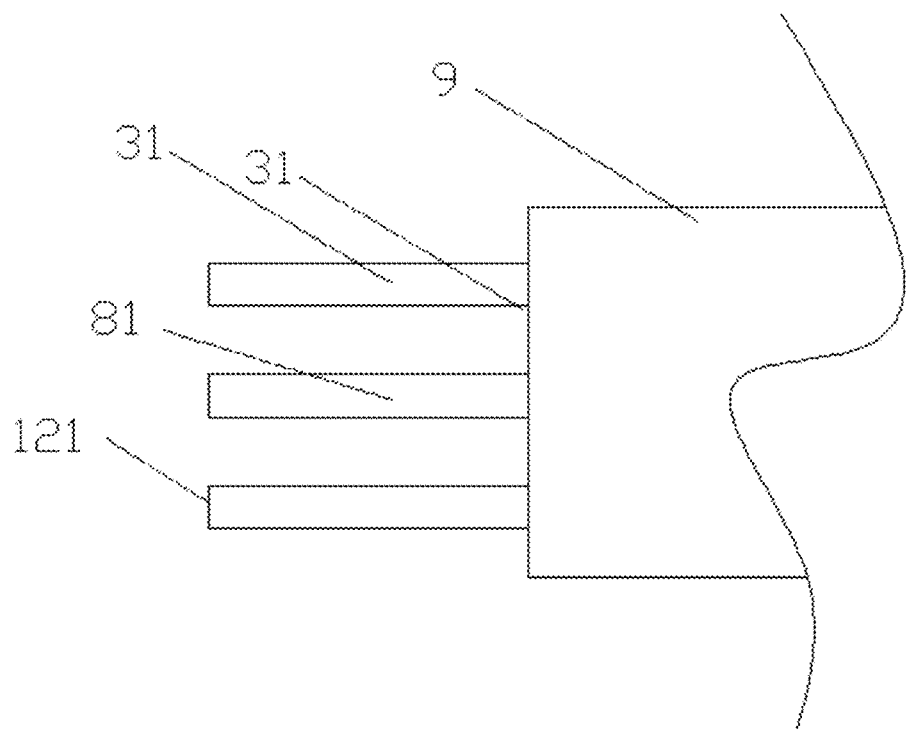
FIG. 7 is a side plane view of the separation mode for preparing three separated catheters, each having the single cavity, according to embodiments of the present disclosure.

A separation mold is configured. A configuration of the separation mold is shown in FIG. 6 and FIG. 7. The separation mold includes a separation mold body 9. The separation mold body 9 is a disk that move forwardly and backwardly. The separation mold body 9 includes three separating tubes 121, 81, and 31 (for trimming to respectively obtain the three catheters 12, 8, and 3, each having the single cavity). Each of the three separating tubes 121, 81, and 31 is a hollow tubular cutter that is arranged vertically on an upper surface of the disk of the mold body 9. A circular center of the hollow tubular cutter corresponds to a circular center of a respective one of the three second cavities 12, 3, and 8. That is, the number of hollow tubular cutters is equal to the number of the three second cavities 12, 3, and 8, each having the single cavity; and positions of the hollow tubular cutters correspond to positions of the three second cavities 12, 3, and 8, each having the single cavity. That is, the circular center of the hollow tubular cutter is aligned to the circular center of the respective one of the three second cavities 12, 3, and 8. A diameter of the hollow tubular cutter is 1 mm greater than the diameter of the respective one of the three second cavities 12, 3, and 8. An opening end of each of the three separating tubes is a sharp blade, and a length of each of the three separating tubes is determined according to a length of the respective one of the three second cavities 12, 3, and 8, that needs to be separated. In some embodiments, the length is 2 cm to 3 cm and is slightly greater than the length of each of the three second cavities 12, 3, and 8 that needs to be separated.

Figure 8:
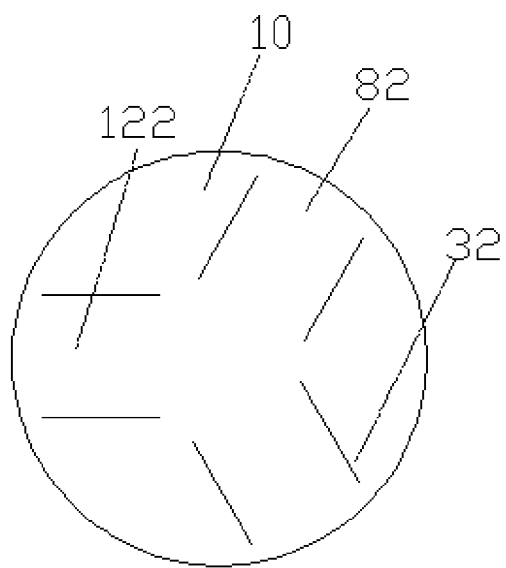
FIG. 8 is a top plane view of a hot-pressing mode for preparing three separated catheters, each having a single cavity, according to embodiments of the present disclosure.
Figure 9:
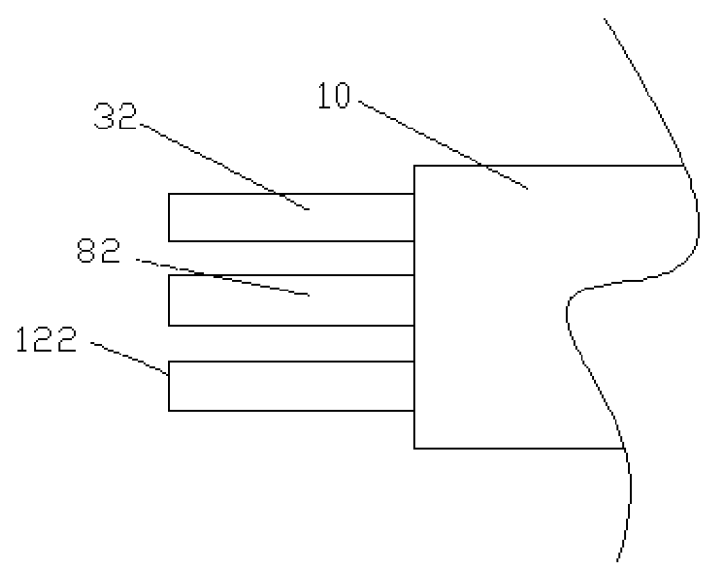
FIG. 9 is a side plane view of the hot-pressing mode for preparing three separated catheters, each having the single cavity, according to embodiments of the present disclosure.

A hot-pressing mold is configured. A configuration of the hot-pressing mold is shown in FIG. 8 and FIG. 9. The hot-pressing mold includes a hot-pressing mold body 10. The hot-pressing mold body 10 is a disk that move forwardly and backwardly. A heating component is arranged inside the disk. The hot-pressing mold body 10 includes three hot-pressing blocks 122, 82, and 32 respectively configured to hot-press the three catheters 12, 8, and 3, each having the single cavity. Each of the three hot-pressing blocks 122, 82, and 32 includes a forward hot-pressing plate and a rear hot-pressing plate, which are arranged perpendicular to an upper surface of the disk of the hot-pressing mold body 10. A geometric center of each set of hot-pressing plates (a center of a rectangle formed by the forward hot-pressing plate and the rear hot-pressing plate) is aligned to the circular center of a respective one of the three second cavities 12, 3, and 8. The number of hot-pressing blocks is equal to the number of the three second cavities 12, 3, and 8, each having the single cavity; and positions of the hot-pressing blocks correspond to positions of the three second cavities 12, 3, and 8, each having the single cavity. The forward hot-pressing plate and the rear hot-pressing plate may be heated by the hot-pressing mold body 10, compressed towards each other. The forward hot-pressing plate and the rear hot-pressing plate may be heated by a method in the related art, where a heating wire is arranged inside each of the forward hot-pressing plate and the rear hot-pressing plate, or a heating wire wraps around a tail portion (a portion inserted into the hot-pressing mold body 10) of each of the forward hot-pressing plate and the rear hot-pressing plate, or an electromagnetic coil wraps around the tail portion of each of the forward hot-pressing plate and the rear hot-pressing plate. The forward hot-pressing plate and the rear hot-pressing plate may be compressed towards each other by a method in the related art, such as compressed by chuck fingers of a lathe; or by hydraulic tong; or by mounting a motor at the tail end of each of the forward hot-pressing plate and the rear hot-pressing plate. Furthermore, the pressure, which is applied to each of the three catheters 12, 3, and 8, each having the single cavity, pressed between the forward hot-pressing plate and the rear hot-pressing plate, can be adjusted by a method available in the related art, such as by the chuck fingers of the lathe or by the hydraulic tongs that can adjust pressures. A length of each of the forward hot-pressing plate and the rear hot-pressing plate is determined according to the length of the respective one of the three second cavities 12, 3, and 8, that needs to be separated. In some embodiments, the length is 2 cm to 3 cm and is slightly greater than the length of each of the three second cavities 12, 3, and 8 that needs to be separated.

Compared to the Embodiment 1, the Embodiment 2 have following characteristics.

In the step 2, as shown in FIGS. 4, 5, 6, and 7, the circular center of each of the three second cavities 12, 8, and 3 of the catheter 1 having the four cavities, which is obtained in the step 1, is aligned to the circular center of the respective one of the three separating tubes 121, 81, and 31 in the separation mold (circular centers alignment). The catheter 1 having the four cavities is moved into the separation mold to reach 2 cm. In this case, the three separating tubes 121, 81, and 31 naturally separates 2 cm from the catheter 1 having the four cavities along the length direction of the catheter 1 to form the three catheters 12, 8, and 3, each having the single cavity; and each of the three catheters 12, 3, and 8 (as shown in FIG. 2 (, each having the single cavity, has the outer wall in the thickness of 0.5 mm. The redundant portion of each of the three catheters 12, 3, and 8, each having the single cavity, is trimmed (the first cavity, i.e., the urinary guiding cavity 2, connected with the body portion of the catheter 1 having the four cavities; and redundant silicone/rubber matrix at the root of each of the three catheters 12, 3, and 8, each having the single cavity, are cut off for 2 cm. Surrounding burrs need to be trimmed to be smooth and flat. In this way, the catheter shown in FIG. 2 is obtained. Precision of trimming in the present step is not required, and trimming in the present step has a greatly improved speed and precision.

In the step 3, each of the three catheters 12, 8, and 3, each having the single cavity, is placed between the forward hot-pressing plate and the rear hot-pressing plate of the respective one of the three hot-pressing blocks 122, 82, and 32. The temperature, the duration, and the pressure are adjusted as described in the Embodiment 1, until each of the three catheters 12, 8, and 3, each having the single cavity, is hot-pressed to be flat. It can be obviously seed that, the top portion of each of the three catheters 12, 3, and 8, each having the single cavity, becomes longer; the inner hollow portion of each of the three catheters 12, 3, and 8 becomes wider. After hot-pressing, an original configuration of each of the three catheters 12, 3, and 8, each having the single cavity (has become three balloons 4, each having the single cavity), is damaged. The outer wall of each of the three catheters 12, 3, and 8, each having the single cavity, become loose. At this moment, each of the three catheters 12, 3, and 8, each having the single cavity, can be easily deformed when being injected with water.

In the step 4, the top ends of the three catheters 12, 3, and 8, each having the single cavity, which are hot-pressed to be flat, are closed (by glue or by hot-melting), and the other operations are the same as those in the Embodiment 1.

According to the present disclosure, special molds are used for preparation. On the one hand, manual work intensity is reduced. On the other hand, in a stage of separating the three catheters 12, 3, and 8, each having the single cavity, and trimming the outer wall of each of the three catheters 12, 3, and 8 to be thinner, the speed and the precision are greatly improved.

Embodiment 3

Compared to the Embodiment 1 and the Embodiment 2, in the Embodiment 3, in order to enable the catheter 1 to be used more conveniently.

Since the strengthening portion is made of metal plating, a lubrication effect is improved, and a front end of the urinary guiding cavity 2 is prevented from being deformed.

In addition, a material of the outer shell is made by mixing with medication or a dye.

Embodiment 4

Compared to the Embodiment 1 and the Embodiment 2, in the Embodiment 4, 2 balloons 2 or 4 balloons are arranged, and technical effects of the catheter 1 in the Embodiment 3 can also be achieved. The corresponding molds only need to be modified accordingly.

What is claimed is:

1. A method of preparing a urinary catheter having a balloon of three cavities at a top end of the urinary catheter, wherein the method comprises:
    Step 1, preparing a catheter having four cavities, cutting one end of the catheter having four cavities to be flat, wherein a first cavity of the four cavities has a circular center located at a circular center of the catheter having four cavities and serves as a urinary guiding cavity; the first cavity has a diameter of 2 mm; the other three cavities of the four cavities serve as three water injection cavities; a circular center of each of the three second cavities is located at a center of a circular radius of a cross section of the catheter having the four cavities; a connection line connecting the circular centers of the three second cavities forms an equilateral triangle; a center or a pendant center of the equilateral triangle is the circular center of the first cavity; each of the three second cavities has a diameter of 0.5 mm;
    Step 2, cutting 2 cm from the one end of the catheter having the four cavities from the catheter longitudinally, along a length direction of the catheter, to form three catheters separated from each other, wherein each of the three catheters has one respective second cavity of the three second cavities; each of the three catheters has a length of 2 cm to 3 cm; each of the three catheters has an outer wall; and a top end of each of the three catheters, each having the one respective second cavity, is closed;
    Step 3, hot-pressing the three catheters by placing each of the three catheters, each having the one respective second cavity, in a steel plate, wherein a front and a rear of the steel plate supply a pressure and heat; a temperature of the hot-pressing is 40° C. to 60° C.; a duration of the hot-pressing is 5 minutes to 15 minutes; a pressure value applied to each of the three catheters, the one respective second cavity, is 5 kg to 7.5 kg; each of the three catheters, each having the one respective second cavity, is pressed to be flat; and a redundant portion of the outer wall of each of the three catheters is trimmed to enable each outer wall to have a thickness of 0.5 mm;

Step 4, connecting each of the top ends of the three catheters, each having the one respective second cavity, to each other by glue or by hot-melting; taking a guide thread to pass through the urinary guiding cavity; wherein the guide thread enters the urinary guiding cavity from a tail end of the urinary guiding cavity and extends out of the urinary guiding cavity from a top portion of the urinary guiding cavity; and after extending out of the urinary guiding cavity, the guide thread is connected to the top ends of the three catheters, each having the one respective second cavity; and Step 5, pressing a water-soluble polymer to form an outer shell, which is hollow and is disposed at the top end of the urinary catheter; coating a tail end of the outer shell with polymer glue; collecting the three catheters, each having the one respective second cavity, to an inside of the outer shell; glueing the tail end of the outer shell to the top end of the catheter having the four cavities, so as to obtain the urinary catheter having the balloon of three cavities at the top end of the urinary catheter.

2. The method according to claim 1, wherein, molds are used to perform the step 2 and the step 3, and the molds comprise: a separation mold, comprising a separation mold body, wherein the separation mold body is a separation disk that is capable of moving forwardly and backwardly; the separation mold body comprises three separating tubes, each of the three separating tubes is a hollow tubular cutter that is arranged vertically on an upper surface of the separation disk of the separation mold body; a circular center of each of the three separating tubes corresponds to the circular center of the respective one second cavity of the three second cavities; a diameter of the hollow tubular cutter is 1 mm greater than the diameter of the respective one second cavity; an opening end of the hollow tubular cutter is a sharp blade having a length of 2 cm to 3 cm;

a hot-pressing mold, comprising a hot-pressing mold body; wherein the hot-pressing mold body is a hot-pressing disk that is capable of moving forwardly and backwardly; a heating component is arranged inside the hot-pressing disk; the hot-pressing mold body comprises three hot-pressing blocks, each of the three hot-pressing blocks comprises a forward hot-pressing plate and a rear hot-pressing plate that are arranged perpendicular to an upper surface of the hot-pressing disk of the hot-pressing mold body; a geometric center of each of the three hot-pressing blocks is aligned to the circular center of the respective one second cavity; each of the three hot-pressing blocks is heated by the hot-pressing mold body and compressed towards each other and is capable of adjusting a pressure applied to a respective one of the three catheters;

wherein the step 2 of the method comprises: aligning the circular center of each of the three second cavities of the catheter having the four cavities, which is obtained in the step 1, to the circular center of the respective one of the three separating tubes in the separation mold; moving the catheter having the four cavities into the separation mold to reach 2 cm to 3 cm; taking the three separating tubes to separate a portion from the catheter having the four cavities to form the three catheters, each having the respective one second cavity of the three second cavities; wherein each of the three catheters, each having the respective one second cavity, has the length of 2 cm to 3 cm and has the outer wall; and the top end of each of the three catheters, each having the respective one second cavity, is closed; wherein the step 3 of the method comprises: placing each of the three catheters, each having the respective one second cavity, between a forward hot-pressing plate and a rear hot-pressing plate of a respective one of the three hot-pressing blocks; wherein the temperature, the duration, and the pressure are applied according to claim 1.

3. The method according to claim 1, wherein a portion of the urinary guiding cavity near the balloon is arranged with a strengthening portion, wherein the strengthening portion is made by performing a metal plating process.

4. The method according to claim 1, wherein a material of the outer shell is made by mixing with medication or a dye.

* * * * *